US010441172B2

(12) United States Patent
Tanaka et al.

(10) Patent No.: US 10,441,172 B2
(45) Date of Patent: Oct. 15, 2019

(54) BRAIN IMAGE RECONSTRUCTION APPARATUS

(71) Applicant: Seiko Epson Corporation, Tokyo (JP)

(72) Inventors: Toshiyuki Tanaka, Matsumoto (JP); Hiroaki Hosomi, Minowa (JP)

(73) Assignee: Seiko Epson Corporation (JP)

( * ) Notice: Subject to any disclaimer, the term of this patent is extended or adjusted under 35 U.S.C. 154(b) by 114 days.

(21) Appl. No.: 15/735,442

(22) PCT Filed: Jul. 29, 2016

(86) PCT No.: PCT/JP2016/003513
§ 371 (c)(1),
(2) Date: Dec. 11, 2017

(87) PCT Pub. No.: WO2017/022228
PCT Pub. Date: Feb. 9, 2017

(65) Prior Publication Data
US 2018/0168452 A1    Jun. 21, 2018

(30) Foreign Application Priority Data

Aug. 5, 2015 (JP) .................................. 2015-154823

(51) Int. Cl.
*G06K 9/00* (2006.01)
*A61B 5/00* (2006.01)
(Continued)

(52) U.S. Cl.
CPC .......... *A61B 5/0042* (2013.01); *A61B 5/0476* (2013.01); *A61B 5/0484* (2013.01);
(Continued)

(58) Field of Classification Search
CPC ... A61B 5/0042; A61B 5/0484; A61B 5/4064; A61B 5/7246; A61B 5/16; A61B 5/0476;
(Continued)

(56) References Cited

U.S. PATENT DOCUMENTS

| 2013/0063550 A1 | 3/2013 | Ritchey et al. |
| 2013/0184558 A1* | 7/2013 | Gallant ................ A61B 5/0042 600/409 |
| 2015/0332016 A1 | 11/2015 | Kamitani et al. |

FOREIGN PATENT DOCUMENTS

| JP | 2014-115913 A | 6/2014 |
| WO | WO-2014-142962 A1 | 9/2014 |

OTHER PUBLICATIONS

Extended European Search Report for Patent Application No. EP16832511.6, dated Feb. 5, 2019 (8 pages).

* cited by examiner

*Primary Examiner* — Andrew M Moyer
(74) *Attorney, Agent, or Firm* — Harness, Dickey & Pierce, P.L.C.

(57) ABSTRACT

A brain image reconstruction apparatus can reconstruct a brain image as a sharper image. A brain image reconstruction apparatus has a data acquisition unit that acquires brain activity data of a user; a brain image reconstructor that detects image information from the brain activity data and constructs a brain image; a linguistic information detector that detects linguistic information from the brain activity data; an image database that stores sample images corresponding to the linguistic information; and an image processor that superimposes the sample image with the brain image, and constructs a process image.

9 Claims, 6 Drawing Sheets

(51) Int. Cl.
    *A61B 5/0476* (2006.01)
    *A61B 5/05* (2006.01)
    *A61B 5/055* (2006.01)
    *A61B 5/16* (2006.01)
    *A61B 5/0484* (2006.01)
    *G06F 3/01* (2006.01)
    *G16H 50/70* (2018.01)
    *G16H 50/20* (2018.01)
    *A61B 5/04* (2006.01)

(52) U.S. Cl.
    CPC ............... *A61B 5/05* (2013.01); *A61B 5/055* (2013.01); *A61B 5/16* (2013.01); *A61B 5/4064* (2013.01); *A61B 5/7246* (2013.01); *A61B 5/04009* (2013.01); *A61B 5/7475* (2013.01); *G06F 3/01* (2013.01); *G06F 3/015* (2013.01); *G06T 2207/10088* (2013.01); *G16H 50/20* (2018.01); *G16H 50/70* (2018.01)

(58) Field of Classification Search
    CPC ....... A61B 5/05; A61B 5/055; A61B 5/04009; A61B 5/7475; G16H 50/70; G16H 50/20; G06T 2207/10088; G06F 3/015; G06F 3/01
    USPC .................................. 382/128–132
    See application file for complete search history.

BRAIN IMAGE RECONSTRUCTION APPARATUS

BACKGROUND

Technical Field

The present invention relates to a brain image reconstruction apparatus.

Related Art

Technology for reconstructing brain images formed in the brain in response to external stimuli has been described (see, for example, U.S. Patent Application Publication No. 2013/0184558). The technology described in U.S. App. Pub. No. 2013/0184558 enables reconstructing brain images of what is recognized in the brain of the user by using brain imaging technology, such as fMRI (functional Magnetic Resonance Imaging), to acquire brain activity data when a person perceives an image visually (through the eyes), and modeling the relationship between the state of brain activity and the object that was observed. By using such technology to reconstruct the brain images of a person that has lost the ability to speak or a person for whom verbal expression is difficult, a third party can recognize what that person is thinking.

However, compared with the brain image formed when actually looking at an object, the brain image formed in the brain when an image is not actually seen is often fragmented or unclear, and the image reconstructed as the brain image of said state is also fragmented or unclear. As a result, it is difficult for a third person viewing the reconstructed image to recognize what the brain image of the user represents, or what the user is thinking. Technology able to reconstruct more clearly defined brain images regardless of whether or not the object is actually being seen is needed.

SUMMARY

The present invention is directed to solving at least part of the foregoing problem as described in the following embodiments and variations.

Example 1 A brain image reconstruction apparatus in this example includes: a data acquisition unit that acquires brain activity data of a user; a brain image reconstructor that detects image information from the brain activity data and constructs a brain image; a non-image information detector that detects non-image information from the brain activity data; an image database that stores sample images corresponding to the non-image information; and an image processor that superimposes the sample image with the brain image, and constructs a process image.

The configuration of a brain image reconstruction apparatus according to this example acquires the brain activity data of a user by the data acquisition unit, and constructs a brain image of the user by the brain image reconstructor. Because the non-image information detector also acquires non-image information from the acquired brain activity data of the user, what is being imagined in the mind of the user can be acquired as non-image information even when the user is not actually viewing the image. Because a sample image corresponding to the detected non-image information is then extracted from an image database, and the image processor constructs a process image by superimposing a sample image with the brain image constructed by the brain image reconstructor, an image that is sharper than the brain image constructed by the brain image reconstructor can be reconstructed. As a result, a third person can more easily recognize what the brain image of the user represents, or more specifically, what the user is thinking.

Example 2 In the brain image reconstruction apparatus described above, the non-image information is preferably linguistic information.

Because this configuration detects linguistic information from the acquired brain activity data of the user, what is being imagined in the mind of the user can be acquired as linguistic information even when the user is not actually viewing the object. As a result, a corresponding sample image can be extracted from the image database based on the linguistic information. In addition, a third person can more easily recognize what the user is thinking by adding the detected linguistic information to the reconstructed brain image, for example.

Example 3 In the brain image reconstruction apparatus described above, a lookup table relates the brain activity data and the non-image information; and the non-image information detector references the lookup table.

This configuration can identify non-image information, such as linguistic information, corresponding to the acquired brain activity data by referencing a lookup table relationally storing brain activity data and non-image information. As a result, a sample image corresponding to the non-image information can be more easily and accurately extracted from the image database.

Example 4 In the brain image reconstruction apparatus described above, any brain imaging technology, including EEG, MEG, fMRI, fNIRS, SPECT, and ECoG, may be used to acquire the brain activity data.

This configuration enables acquiring brain activity data of a user using any brain imaging technology, including EEG, MEG, fMRI, fNIRS, SPECT, and ECoG.

Example 5 In the brain image reconstruction apparatus described above, an image display preferably displays the brain image constructed by the brain image reconstructor, the non-image information detected by the non-image information detector, and the process image constructed by the image processor.

This configuration enables a third person to more accurately recognize what the user is thinking by displaying the constructed brain image, linguistic information or other non-image information, and a process image superimposing a sample image on the brain image. Furthermore, by displaying these images on the image display, the user can see and verify the brain image constructed from the user's own brain activity data, the non-image information, and the process image.

Example 6 In the brain image reconstruction apparatus described above, an image compensation unit preferably reacquires brain activity data of the user when viewing the process image displayed on the image display, and corrects the process image based on the reacquired brain activity data.

This configuration can reconstruct the brain image as a sharper image by reacquiring brain activity data of the user when viewing the process image displayed on the image display, and the image compensation unit correcting the process image based on the reacquired brain activity data.

Example 7 In the brain image reconstruction apparatus described above, the image display can display selection options including plural different process images for the acquired brain activity data; and the brain image reconstruction apparatus has an interface unit including the image display and an operating unit enabling the user to select the desired process image from the selection options.

This configuration can more accurately reconstruct the brain image of the user because the interface unit displays, on the image display, selection options including plural different process images constructed for the acquired brain activity data, and the user can use the operating unit to select the desired process image from the displayed selection options.

Example 8 The brain image reconstruction apparatus described above further preferably connects to an external device that stochastically or statistically constructs the selection options based on the acquired brain activity data.

This configuration can stochastically or statistically construct, on an external device connected to the brain image reconstruction apparatus, selection options based on the acquired brain activity data. Because selection options that are more reliable and frequently occurring can thus be provided, what the user is thinking can be recognized more accurately. Furthermore, by offloading the function of creating the selection options to an external device, recognition accuracy can be improved while the configuration of the brain image reconstruction apparatus can be simplified.

Example 9 In the brain image reconstruction apparatus described above, the process images are displayed as selection options on the image display in descending order of stochastic or statistical likelihood by collecting and interpreting brain activity data acquired in the past from the user.

By accumulating and interpreting brain activity data acquired in the past from a specific user, and displaying process images in descending order of stochastic or statistical likelihood, this configuration can provide the user with more accurate or frequently occurring selection options.

DETAILED DESCRIPTION

Figure 1:
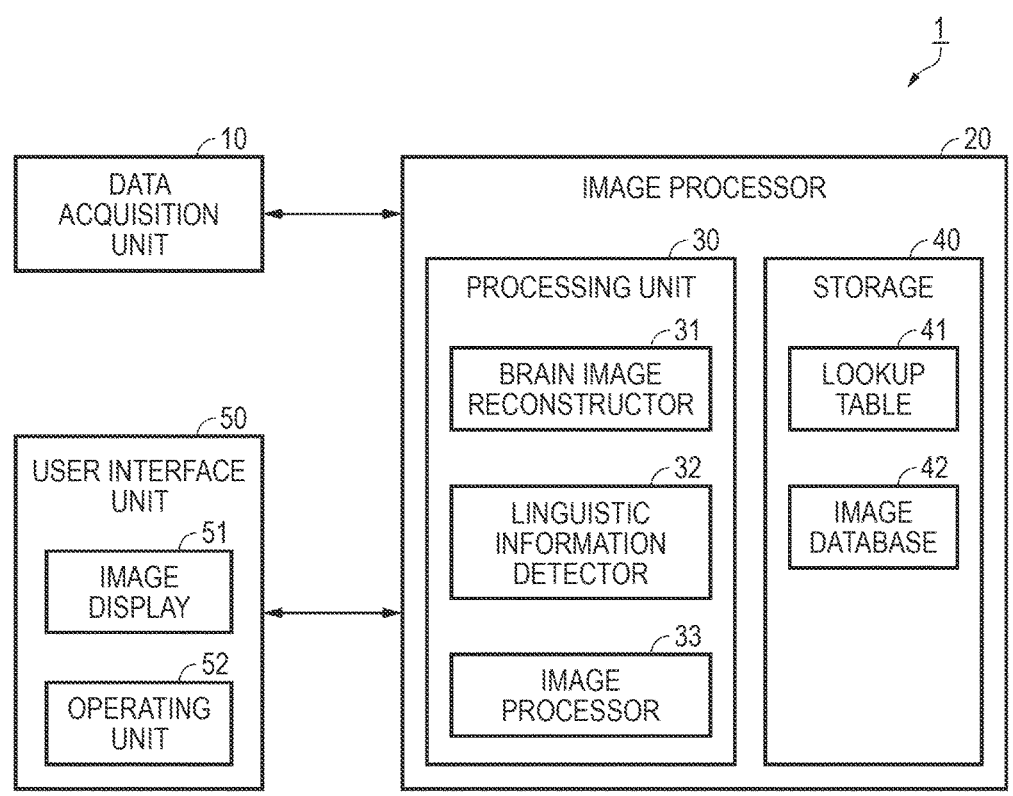
FIG. 1 is a block diagram illustrating the configuration of a brain image reconstruction apparatus according to a first embodiment of the invention.

An objective of this embodiment of the invention is to provide a brain image reconstruction apparatus that supports communication between a third person, and a user that has lost speech-related function or a user that has difficulty with verbal expression (referred to below as simply the "user"). More specifically, the invention enables more clearly reconstructing as an image the object perceived in the brain of the user (and if possible, including the situation in which the object is located). A "third person" as used herein supposes a person that communicates with the user and has normal speech function, but may be another user.

Technology enabling reconstructing brain images is disclosed in U.S. App. Pub. No. 2013/0184558 assigned to The Regents Of The University Of California. This technology enables reconstructing a brain image recognized in the brain of the user by acquiring brain activity data when the user perceives an object by vision (through the eyes), and modeling the relationship between the state of brain activity and the object that was viewed. In addition, JP-T-2012-522559 discloses technology for visualizing dreams seen by a sleeping person.

The brain image reconstruction apparatus of this invention is based on technology disclosed in U.S. App. Pub. No. 2013/0184558, and is an apparatus for detecting image information and constructing a brain image from acquired brain activity. The brain image reconstruction apparatus according to the invention also detects non-image information, recognizes from the non-image information what is imagined in the brain of the user, and reconstructs a clearer brain image. Note that non-image information as used herein is information other than image information that enables recognizing an object conceptually, and more specifically is information related to linguistic information such as the name of an object, information that appeals to the five senses other than vision, specifically taste, touch, hearing, and smell, temperature information such as hot and cold, and information related to emotions such as like, dislike, and fear.

An outline of the brain image reconstruction method of the invention is described first. Using the example of images seen in a dream of a sleeping person, and more particularly in this example when seeing a dream of being bitten by a dog, even if the size or color of the dog, the sound of the dog's bark, and other features seen in the dream are remembered, memories of such details as the shape of the dog or the background around the dog, may not remain. Features of the dog seen in the dream may also remain only in fragments.

Consider this in terms of data processing by the brain. In images that are actually seen by a person, data is processed in the visual cortex of the occipital lobe with high resolution down to such detail as the shape of objects and the background. The brain then recognizes the high resolution images that are processed by the brain, and can recognize that the object is a dog, the overall image and features of the object, and even the surroundings. It is thought that the object, background, and the rest of the entire image seen in a dream while sleeping are not processed with the same high resolution as images that are actually seen (that is, do not require processing at high resolution), but the brain can still recognize that the object seen in a dream is a dog.

We then hypothesized that this might be due to the brain determining what the object is not only from images formed in the visual cortex of the brain while dreaming, but by also conceptualizing the object seen in the dream. In other words, we thought that when seeing a dog in a dream, the brain does not recognize the object dog as a high resolution image of the shape, for example, but simplifies processing the detailed shape recognition of the dog by conceptualizing and recognizing the object by the word "dog."

This theory may apply not only to when a sleeping person is seeing a dream, but also to what an awake person is thinking. More specifically, imagining something involves a person not only forming an image in the visual cortex of the brain, but also applying conceptual information (such as linguistic information) to the object being imagined.

According to this theory, a brain image constructed in someone's head is fragmented and vague compared with the brain image formed when the object is actually seen, and even if the brain image that is imagined is reconstructed with great accuracy, the image will not be as clear as when the object is actually seen. In this case, it will be difficult for a third person viewing the reconstructed brain image of that person to recognize what the brain image of that person represents, or more specifically, what that person is thinking.

For example, JP-A-2014-115913 describes technology for acquiring and outputting object information such as the name of an object from the brain activity information of a person (test subject). This technology enables acquiring linguistic information from brain activity data. Because what an object is can be recognized if linguistic information can be acquired from brain activity data, the general shape of an object can be predicted based on the linguistic information.

We therefore theorized that a sharper brain image could be reconstructed by superimposing sample images of objects selected based on linguistic information acquired from brain activity data on the brain image constructed by detecting image information from conventional brain activity data. Specific embodiments of the invention are described below with reference to the figures.

Embodiment 1

Configuration of a Brain Image Reconstruction Apparatus

The configuration of a brain image reconstruction apparatus according to the first embodiment of the invention is described with reference to FIG. 1. FIG. 1 is a schematic block diagram illustrating the configuration of a brain image reconstruction apparatus according to the first embodiment of the invention. A brain image reconstruction apparatus 1 according to the first embodiment is an apparatus that reconstructs brain images recognized in the brain of a person. Note that herein an "image" is not limited to still images (pictures), and includes moving images (video). A brain image reconstructed by the brain image reconstruction apparatus 1 therefore refers primarily to still pictures, but may also involve motion.

As shown in FIG. 1, the brain image reconstruction apparatus 1 has a data acquisition unit 10, image processor 20, and user interface unit 50. The data acquisition unit 10 and user interface unit 50 are connected to the image processor 20 through an interface (not shown in the figure).

The data acquisition unit 10 functions to acquire brain activity data from a user. The data acquisition unit 10 may be embodied by devices using appropriate brain imaging technologies such as EEG (Electroencephalogram), MEG (Magnetoencephalography), fMRI (functional Magnetic Resonance Imaging), fNIRS (functional Near-Infrared Spectroscopy), SPECT (Single Photon Emission Computed Tomography), and ECoG (Electrocorticogram).

The image processor 20 has a function of reconstructing brain images based on image information and non-image information (specifically, linguistic information) detected from the brain activity data acquired by the data acquisition unit 10. The image processor 20 has a processing unit 30 and storage 40. The processing unit 30 includes a brain image reconstructor 31, a linguistic information detector 32 as a non-image information detection unit, and an image processor 33. The brain image reconstructor 31 detects image information from brain activity data and constructs a brain image using technology disclosed in U.S. App. Pub. No. 2013/0184558.

The linguistic information detector 32 references a lookup table 41 described below, and detects linguistic information from the brain activity data. The linguistic information detected here is primarily the name of an object, and may include information related to an operation of an object or the situation in which the object is present. The image processor 33 acquires, from an image database 42 described below, a sample image corresponding to the linguistic information detected by the linguistic information detector 32, and constructs a process image superimposing the sample image on the brain image constructed by the brain image reconstructor 31. The process image constructed by the image processor 33 is output as the reconstructed brain image of the user.

The processing unit 30 includes a CPU (Central Processing Unit), ROM (Read Only Memory), and RAM (Random Access Memory), not shown. The processing unit 30 writes a control program stored in ROM to RAM, for example, and operates as the parts of the processing unit 30 by the CPU executing the control program rendered in RAM. Alternatively, the processing unit 30 may be configured with hardware such as an ASIC (Application Specific IC) embodying the same functionality achieved by the CPU executing a control program, or by a combination of a CPU and ASIC.

The storage 40 stores a lookup table 41 and image database 42. Brain activity data and linguistic information are relationally stored in the lookup table 41 based on previously collected brain activity data. The image database 42 stores sample images corresponding to the linguistic information stored in the lookup table 41. The storage 40 is configured with nonvolatile memory such as EEPROM (Electrically Erasable Programmable Read Only Memory), and nonvolatilely, rewritably stores information.

The image processor 20 is not limited to a specific hardware configuration, can be desirably configured from hardware and software, and may be an external device such as a cloud server in a cloud system.

The user interface unit 50 includes an image display 51 and an operating unit 52. The image display 51 displays the process image constructed by the image processor 33 as a reconstructed brain image. This enables showing a third person what the user is thinking about. The user can also see a brain image constructed from the user's own brain activity data. The image display 51 is a display device such as an LCD (Liquid Crystal Display) panel or OLED (Electroluminescence Display) panel.

The image display 51 may also display the brain image constructed by the brain image reconstructor 31, and the linguistic information detected by the linguistic information detector 32. This configuration enables a third person to recognize more accurately what the user is thinking, and enables the user to see and check the brain image constructed from the user's own brain activity data, the linguistic information, and the process image.

The operating unit 52 may be configured with buttons, keys, or a touch panel, for example. When the operating unit 52 is configured with a touch panel, the image display 51 and operating unit 52 may be integrated as a single device. The user interface unit 50 may, for example, be a mobile terminal connected as a client to a cloud server rendering the function of the image processor 20.

Brain Image Reconstruction Method

The brain image reconstruction method of a brain image reconstruction apparatus 1 according to the first embodiment of the invention is described next. A lookup table 41 and image database 42 are previously compiled by the brain image reconstruction apparatus 1. First, sample images of various objects are prepared. The sample images are preferably images of similar objects, or more specifically, sample images of multiple objects that may be represented by the same linguistic information but have features that are different from each other.

Figure 2:
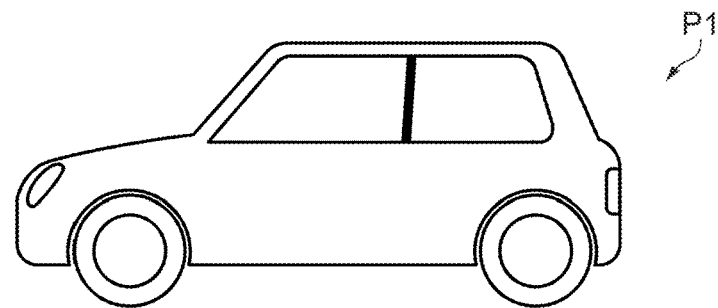
FIG. 2 shows an example of a sample image stored in an image database.
Figure 3:
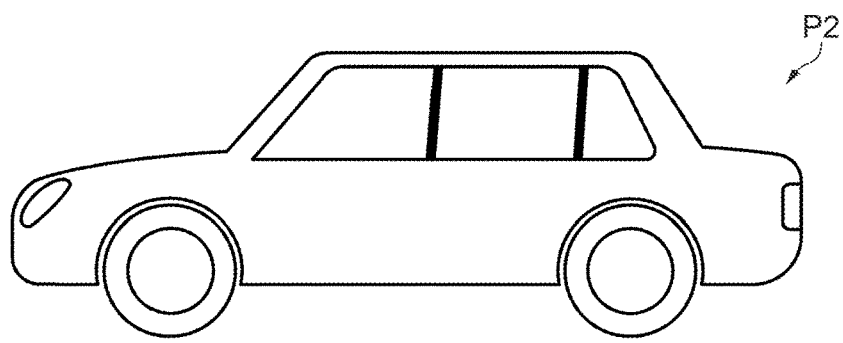
FIG. 3 shows an example of a sample image stored in an image database.
Figure 4:
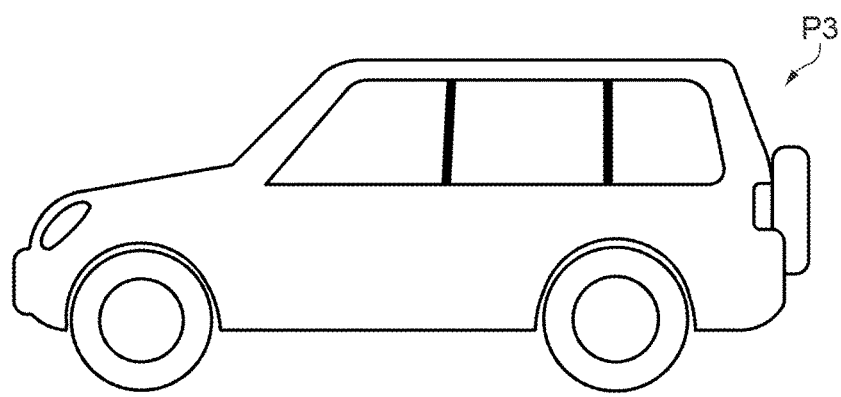
FIG. 4 shows an example of a sample image stored in an image database.

FIG. 2, FIG. 3, and FIG. 4 show examples of sample images stored in the image database. FIG. 2, FIG. 3, and FIG. 4 show images P1, P2, P3 as examples of sample images of automobiles as an example of similar objects with different features. Note that the sample images are primarily still images, but may also include some movement (rising, fall, for example), state change (deformation, rupture, for example) or other object motion.

Next, the prepared sample images are shown to the user (test subject), who is then requested to express linguistic information (the name) identifying the object shown in the sample image. The linguistic information is preferably expressed by the user speaking the name of the object, but may be expressed by writing or keyboard input, and the method of expression may be selected from among prepared options.

The brain activity data of the user when expressing by linguistic information the object shown in the sample image is acquired for each sample image. The brain activity data acquired for one sample image is then relationally stored in the lookup table 41 to the linguistic information expressed for that sample image. The sample image and expressed linguistic information are also relationally stored in the image database 42. The lookup table 41 and image database 42 are compiled in the storage 40 of the brain image reconstruction apparatus 1 by repeating these steps.

Figure 5:
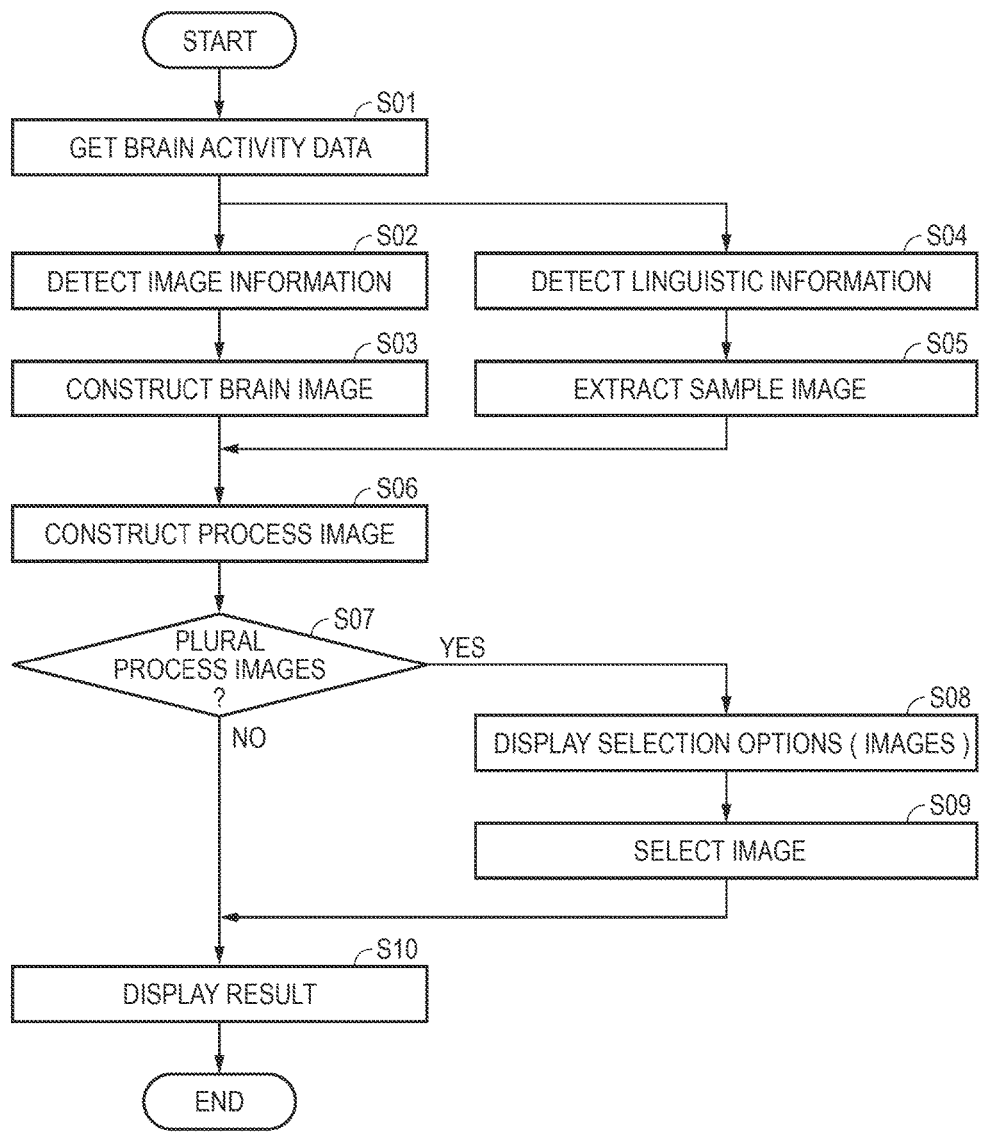
FIG. 5 is a flow chart of the brain image reconstruction process of the brain imaging reproduction apparatus according to the first embodiment of the invention.
Figure 6:
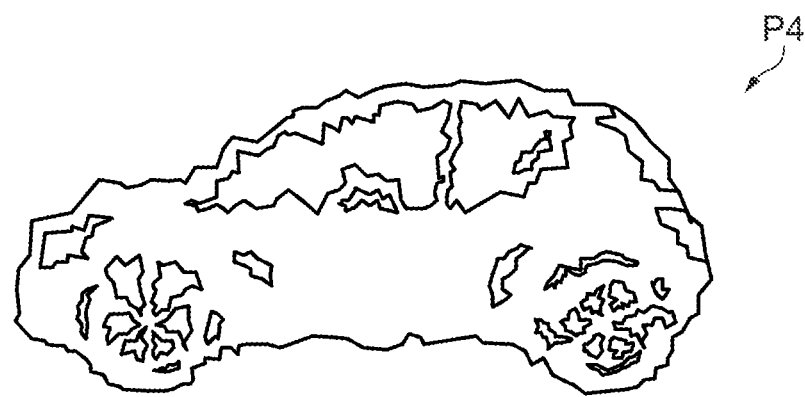
FIG. 6 shows an example of a brain image formed by the brain image reconstructor.
Figure 7:
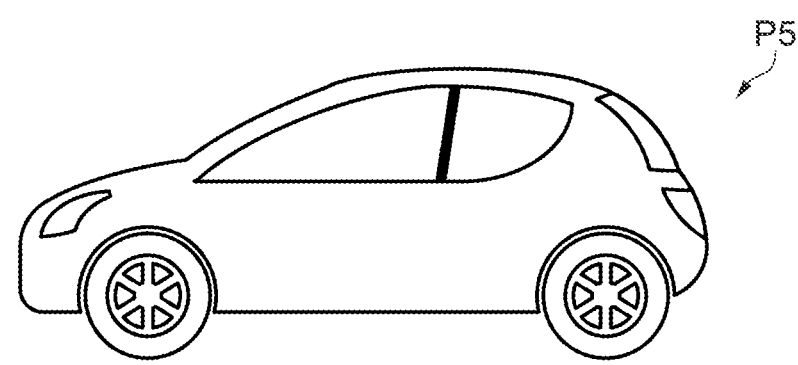
FIG. 7 shows an example of a processed image produced by the image processor.

The method of using the brain image reconstruction apparatus 1 according to the first embodiment of the invention to reconstruct a brain image of the user is described next. FIG. 5 is a flow chart describing the brain image reconstruction method of the brain image reconstruction apparatus according to the first embodiment of the invention. FIG. 6 shows an example of a brain image formed by the brain image reconstructor. FIG. 7 shows an example of a process image constructed by the image processor.

First, the data acquisition unit 10 acquires the brain activity data of the user (step S01). Next, the brain image reconstructor 31, based on the technology disclosed in U.S. App. Pub. No. 2013/0184558, detects image information from the brain activity data acquired by the data acquisition unit 10 (step S02). A brain image is then constructed from the detected image information (step S03). In this example, the image P4 shown in FIG. 6 was constructed as the brain image.

The linguistic information detector 32 also detects linguistic information from the brain activity data acquired by the data acquisition unit 10 (step S04). The linguistic information may be detected as follows. The linguistic information detector 32 compares the acquired brain activity data with the brain activity data stored in the lookup table 41, and extracts the brain activity data determined to have a specific similarity to the acquired brain activity data.

If there is a specific similarity to multiple instances of brain activity data in the lookup table 41, the brain activity data with the greatest similarity is extracted. The linguistic information detector 32 then references the lookup table 41 to detect the linguistic information corresponding to the extracted brain activity data. In this example, Automobile is detected as the linguistic information corresponding to the brain activity data.

Next, the image processor 33 extracts, from the sample images stored in the image database 42, the sample image corresponding to the linguistic information detected by the linguistic information detector 32 (step S05). Because Automobile is detected as the linguistic information corresponding to the brain activity data in this example, the multiple sample images P1, P2, P3 shown in FIG. 2, FIG. 3, and FIG. 4 are retrieved.

In step S05, the image processor 33 extracts the sample image with the greatest similarity to the brain activity data constructed by the brain image reconstructor 31. The similarity between the brain image and sample images may be evaluated by, for example, detecting similarities based on the external shape or pattern of the object, or the size and relative locations of blank spaces and openings, and comparing the number of similarities, or the size of the range of similar parts. In this example, sample image P1 in FIG. 2 is selected from the sample images P1, P2, P3 in FIG. 2, FIG. 3, and FIG. 4.

Next, the image processor 33 constructs a process image by superimposing the sample image extracted from the image database 42 with the brain image constructed by the brain image reconstructor 31 (step S06). Processing the image is done by, for example, identifying similar parts in the brain image and sample image; and in areas other than the similar parts, leaving that part of the brain image in areas of the brain image that are relatively clear, and substituting that part of the sample image for parts that are not clear. In this example, the process image P5 shown in FIG. 7 is constructed by superimposing the sample image P1 shown in FIG. 2 with the image P4 shown in FIG. 6.

If multiple sample images corresponding to the linguistic information are found, and multiple sample images with a strong resemblance to the brain image constructed by the brain image reconstructor 31 are extracted from those images in step S05, multiple process images are constructed by superimposing the multiple sample images extracted from the image database 42 with the brain image in step S06. Next, whether or not multiple process images were constructed by the image processor 33 is determined (step S07).

If there are multiple process images (step S07: YES), selection options (multiple process images) are displayed on the image display (step S08). By looking at the image display 51 and using the operating unit 52, the user selects from the displayed choices the process image that is closest to the image in the mind of the user (step S09). That result is then displayed on the image display 51 (step S10). If the image processor 33 did not construct multiple process images (step S07: NO), the process image that was constructed is displayed as the result on the image display 51 (step S10).

While it is difficult to recognize what the object is from the image P4 constructed by the brain image reconstructor 31 and shown in FIG. 6, that the object in the process image P5 shown in FIG. 7 is an Automobile, and distinguishing features, are clear. A third person can also know what the user is thinking by looking at the process image displayed on the image display 51. As a result, the user and a third person (or two users) can communicate.

Note that, in step S04, if there are multiple instances of brain activity data in the lookup table 41 with equivalently strong similarity to the acquired brain activity data, plural different instances of linguistic information corresponding to the plural instances of brain activity data may be retrieved, and the plural instances of linguistic information, or sample images corresponding to the linguistic information, may be displayed as candidates for selection by the user.

Alternatively in step S10, the brain image constructed by the brain image reconstructor 31 (image P4 shown in FIG. 6), the linguistic information detected by the linguistic information detector 32, and the process image (process image P5 in FIG. 7) constructed by the image processor 33, may be displayed on the image display 51. When, for example, a third person cannot recognize the object from the final process image, this configuration enables the third person to recognize the object by combining the brain image with the linguistic information.

If, for example, the object shown in the final process image differs from what the user was thinking, whether or not the correct linguistic information was detected from the brain activity data can be verified by displaying the detected linguistic information. If the correct linguistic information was not detected from the brain activity data, extracting the sample image in step S05, and constructing the process image in step S06, may be repeated by inputting the correct linguistic information from the operating unit 52. The correlation between brain activity data and linguistic information in the lookup table 41 can also be adjusted by inputting the correct linguistic information from the operating unit 52 when the correct linguistic information was not detected from the brain activity data.

As described above, the brain image reconstruction apparatus 1 according to the first embodiment of the invention detects linguistic information from the acquired brain activity data of a user, and constructs a process image overlaying the sample image corresponding to the detected linguistic information with the brain image constructed from the brain activity data, and can therefore reconstruct the brain image as a sharper image. As a result, what the brain image of a user represents, that is, what the user is thinking, can be easily recognized by a third person.

Embodiment 2

Configuration of a Brain Image Reconstruction Apparatus

Figure 8:
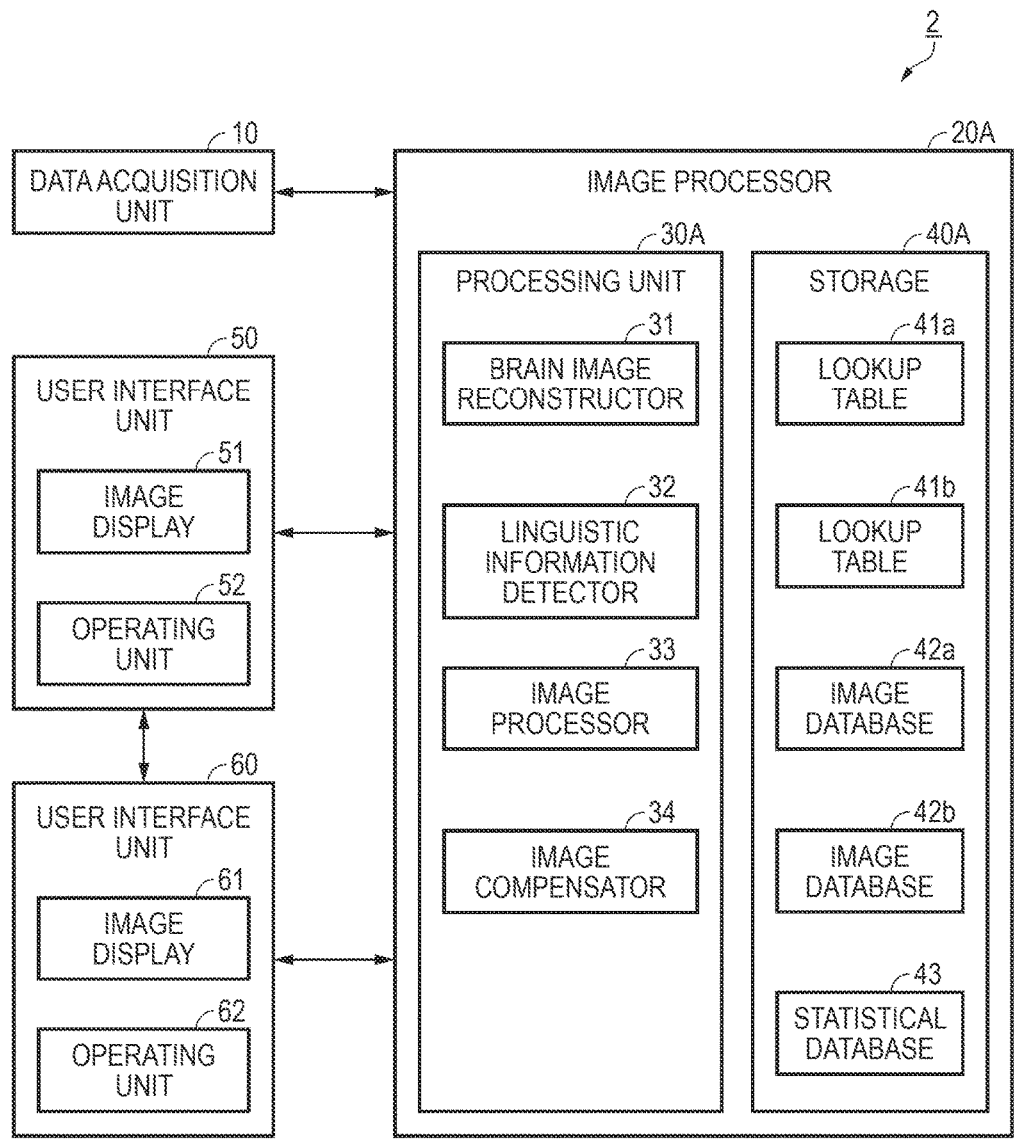
FIG. 8 is a block diagram illustrating the configuration of a brain image reconstruction apparatus according to a second embodiment of the invention.

The configuration of a brain image reconstruction apparatus according to a second embodiment of the invention is described with reference to FIG. 8. FIG. 8 is a schematic block diagram illustrating the configuration of a brain image reconstruction apparatus according to a second embodiment of the invention. As shown in FIG. 8, the brain image reconstruction apparatus 2 according to the second embodiment of the invention has a data acquisition unit 10, image processor 20A, user interface unit 50, and user interface 60. The data acquisition unit 10, user interface unit 50, and user interface 60 are connected to the image processor 20A through an interface (not shown in the figure). Differences between this and the first embodiment are described below, like parts in this and the first embodiment are identified by like reference numerals, and further description thereof is omitted.

The image processor 20A has a processing unit 30A and storage 40A. The processing unit 30A includes a brain image reconstructor 31, linguistic information detector 32, an image processor 33, and an image compensator 34. The image compensator 34 functions to correct details in the process image constructed by the image processor 33. For example, when part of the object shown in the final process image is not clear, or differs in part from what the user was thinking, that part can be corrected. As a result, the brain image reconstruction apparatus 2 according to the second embodiment of the invention can reconstruct the brain image of the user as an even sharper, more accurate image.

Correcting the process image may be done by, for example, the user specifying the parts that are not clear, or parts that need correcting, in the process image displayed on the image display 51, and selecting the type of correction to apply from among options (such as enlarging or reducing parts, or adding, deleting, or replacing parts) displayed on the image display 51. Further alternatively, other sample images or candidates suitable to correcting a particular part may be searched for and displayed for the parts that require correction.

The storage 40A stores multiple lookup tables (two in this example, lookup table 41a and lookup table 41b), multiple image databases (two in this example, image database 42a and image database 42b), and a statistical database 43. There may also be three or more lookup tables and image databases.

By maintaining multiple lookup tables, lookup table 41a and lookup table 41b, one may be used as a basic table and the other as a user table specific to a certain user. Lookup table 41a and lookup table 41b may also be tables specific to two different users.

By maintaining two image databases, image database 42a and image database 42b, sample images may be stored in one, while final process images (included corrected images) are stored in the other. In this case, the acquired brain activity data and the final process image may be relationally stored in the lookup table 41a (or 41b). By accumulating past process images, this configuration also enables extracting a final process image from newly acquired brain activity data.

Stored in the statistical database 43 is statistical data, such as the linguistic information detected for brain activity data acquired in the past, the sample images selected for that linguistic information, and the process image (including corrected images) that was finally acquired. In other words, thought patterns and interests unique to the user can be learned by the user repeatedly using the brain image reconstruction apparatus 2.

As a result, the brain image reconstruction apparatus 2 according to the second embodiment of the invention can increase the goodness-of-fit of the correlation between the brain activity data and linguistic information to the brain activity data acquired by the data acquisition unit 10. The sample images may then be displayed in descending order from the images selected most frequently in the past, or from the images with the highest probability of selection, as the process image candidates. In this event, the sample image with the highest frequency of past selection may be displayed larger than the other candidate images, or the process image with the highest probability of matching may be displayed larger than the other process images.

Furthermore, if the brain activity data acquired in the past includes brain activity data for which the same process image (including corrected images) has been acquired with great frequency, when brain activity data that is the same as that specific instance of brain activity data is acquired, the process image (including corrected images) acquired in the past for that specific brain activity data may be displayed as a candidate.

Like the user interface unit 50, the user interface 60 includes a image display 61 and operating unit 62. The brain image reconstruction apparatus 2 according to the second embodiment of the invention enables a user and a third person (or second user) in a separate location to communicate by, for example, the user using user interface unit 50, and the third person (or other user) using user interface 60.

Brain Image Reconstruction Method

Figure 9:
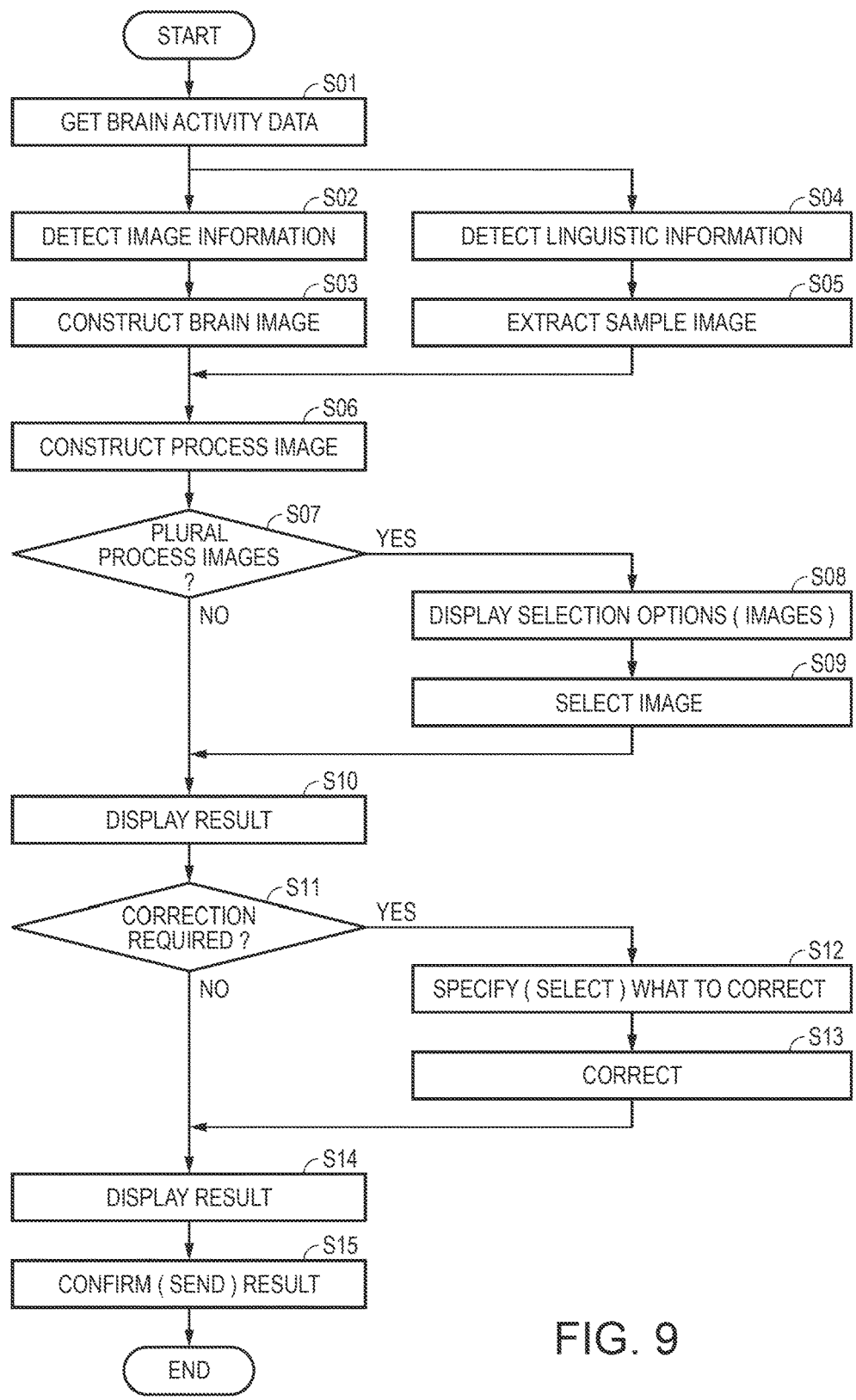
FIG. 9 is a flow chart of the brain image reconstruction process of the brain imaging reproduction apparatus according to the second embodiment of the invention.

The brain image reconstruction method of a brain image reconstruction apparatus according to the second embodiment of the invention is described next. FIG. 9 is a flow chart describing the brain image reconstruction method of the brain image reconstruction apparatus according to the second embodiment of the invention. Differences between this and the first embodiment are described below, like steps in this and the first embodiment are identified by like reference numerals, and further description thereof is omitted.

After step S10 in the second embodiment, the user is prompted to determine if correction of the process image displayed on the image display 51 in step S10 is required (step S11). If the user determines correction is required (step S11: YES), the user specifies (or selects) where correction is required and what correction is required through the user interface unit 50 or user interface 60 (step S12). Based on the content of the correction specified (or selected) by the user, the process image is then corrected (step S13).

The image resulting from the correction is then displayed on the image display 51 (step S14). If the user determines correction is not required (step S11: NO), the process image displayed in step S10 is displayed on the image display 51 as the final process image.

When the user confirms the corrected image (the process image when correction is unnecessary), the result is confirmed and sent to the image processor 20A (step S15). As a result, the corrected image finally acquired for the brain activity data acquired in step S01 (the process image when correction is unnecessary) is stored in the image database 42a (or 42b).

If the user corrects the linguistic information related to the brain activity data acquired in step S01, the corrected linguistic information is stored relationally to the brain activity data in the lookup table 41a (or 41b). The linguistic information, sample image, and process image (including corrected image) for the brain activity data is then stored as statistical data in the statistical database 43.

As described above, because the brain image reconstruction apparatus 2 according to the second embodiment of the invention can correct details in the constructed process image, the brain image of the user can be reconstructed as an even sharper, more accurate image. Furthermore, by collecting past statistical data, an image with a high probability of fit can be selected and displayed as the brain image matching the acquired brain activity data. As a result, because what the user is thinking can be more easily recognized by another party, the user and a third person (or two users) can communicate more smoothly.

The invention is described above with reference to preferred embodiments thereof, but the invention is not limited thereto and can be modified and adapted in many ways without departing from the scope of the accompanying claims. Some variations are described below.

Variation 1

In the brain image reconstruction apparatuses 1, 2 described above, the linguistic information detector 32 may detect multiple instances of linguistic information from the acquired brain activity data. When multiple instances of linguistic information are detected, multiple objects may be included in the brain image of the user, or the background may be an important element in addition to the main object. In this case, if a sample image is extracted for each instance of detected linguistic information, and the brain image constructed by the brain image reconstructor 31 is processed by superimposing each of the sample images, multiple objects and the background in the brain image of the user can be reconstructed more clearly.

Variation 2

For the image compensator 34 in the brain image reconstruction apparatus 2 to correct the process image, the brain activity data of the user when viewing the uncorrected process image may be acquired, and correction may be applied using the brain image constructed from the re-acquired brain activity data. This configuration enables correcting the image to reflect the reaction of the user to the process image.

Variation 3

When the user and the person (third person) communicating with the user can communicate by normal spoken language, brain activity data may also be acquired from the third person and a brain image reconstructed, and the reconstructed brain image of the third person may also be displayed on the image display 51 of the user interface unit 50. In this case, even smoother communication can be achieved because each can view the brain image of the other.

Variation 4

The brain image reconstruction apparatus 1, 2 described above supports communication with people that cannot speak, and people with aphasia or other speech impairment, but can also be used in other fields. For example, reconstructing images from the memories of people that have been in an accident or saw a crime; creating a picture of a vague idea; and expressing as an image a thought that the user cannot express well with words. The invention can also be used to record dreams while under hypnosis during psychological counseling, or when wanting to communicate with a person that is in a coma and unable to talk.

Variation 5

Non-image information is described below as it relates to non-linguistic information such as the name of an object. When the image information detected from the brain activity data of a user is a red circle, it is unclear from the image information alone what the object is. In this case, the object is known to be a red apple if information indicating the name Apple can be detected, but the object can still be guessed to be an apple if flavor information such as "sweet and tart" can be detected even if the name cannot be detected.

If a Mountain can be detected from the image information, and Cold can be detected as sensory (temperature) information, the image can be recognized as a mountain in winter instead of a mountain in summer.

More accurate communication can thus be enabled by using non-image information in addition to image information.

The entire disclosure of Japanese Patent Application No. 2015-154823 filed on Aug. 5, 2015 is expressly incorporated by reference herein.

The invention claimed is:

1. A brain image reconstruction apparatus comprising:
   a data acquisition unit that acquires brain activity data of a user;
   a brain image reconstructor that detects image information from the brain activity data and constructs a brain image;
   a non-image information detector that detects non-image information from the brain activity data;
   an image database that stores sample images corresponding to the non-image information; and
   an image processor that superimposes the sample image with the brain image, and constructs a process image.

2. The brain image reconstruction apparatus described in claim 1, wherein:
the non-image information is linguistic information.

3. The brain image reconstruction apparatus described in claim 1, wherein:
a lookup table relates the brain activity data and the non-image information; and
the non-image information detector references the lookup table.

4. The brain image reconstruction apparatus described in claim 1, wherein:
any brain imaging technology, including EEG, MEG, fMRI, fNIRS, SPECT, and ECoG, is used to acquire the brain activity data.

5. The brain image reconstruction apparatus described in claim 1, further comprising:
an image display that displays the brain image constructed by the brain image reconstructor, the non-image information detected by the non-image information detector, and the process image constructed by the image processor.

6. The brain image reconstruction apparatus described in claim 5, further comprising:
an image compensation unit that reacquires brain activity data of the user when viewing the process image displayed on the image display, and corrects the process image based on the reacquired brain activity data.

7. The brain image reconstruction apparatus described in claim 5, wherein:
the image display can display selection options including plural different process images for the acquired brain activity data;
an interface unit includes the image display, and an operating unit enabling the user to select the desired process image from the selection options.

8. The brain image reconstruction apparatus described in claim 7, wherein:
the brain image reconstruction apparatus connects to an external device that stochastically or statistically forms the selection options based on the acquired brain activity data.

9. The brain image reconstruction apparatus described in claim 8, wherein:
the process images are displayed as selection options on the image display in descending order of stochastic or statistical likelihood by collecting and interpreting brain activity data acquired in the past from the user.

* * * * *